United States Patent
Higami et al.

(10) Patent No.: US 12,403,219 B2
(45) Date of Patent: Sep. 2, 2025

(54) METHOD FOR PRODUCING DECELLULARIZED MATERIAL FOR TRANSPLANTATION AND GRAFT COMPOSITION CONSISTING OF BIOCOMPATIBLE MATERIAL INCLUDING SAID MATERIAL

(71) Applicant: ADEKA CORPORATION, Tokyo (JP)

(72) Inventors: Tetsuya Higami, Hyogo (JP); Kenichiro Hiwatari, Tokyo (JP); Yu Yamaguchi, Tokyo (JP); Haruki Obara, Tokyo (JP); Takuya Kimura, Tokyo (JP); Mitsumasa Homma, Tokyo (JP); Kyohei Ochiai, Tokyo (JP); Keita Kinoshita, Tokyo (JP); Naoki Morimoto, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 712 days.

(21) Appl. No.: 16/615,177

(22) PCT Filed: May 25, 2018

(86) PCT No.: PCT/JP2018/020141
§ 371 (c)(1),
(2) Date: Nov. 20, 2019

(87) PCT Pub. No.: WO2018/221402
PCT Pub. Date: Dec. 6, 2018

(65) Prior Publication Data
US 2020/0222589 A1 Jul. 16, 2020

(30) Foreign Application Priority Data
May 30, 2017 (JP) .................... 2017-106400

(51) Int. Cl.
*A61L 27/36* (2006.01)
*A61L 27/50* (2006.01)

(52) U.S. Cl.
CPC ....... *A61L 27/3691* (2013.01); *A61L 27/3625* (2013.01); *A61L 27/507* (2013.01); *A61L 2430/40* (2013.01)

(58) Field of Classification Search
CPC ............. A61L 27/3691; A61L 27/3625; A61L 27/507; A61L 2430/40
(Continued)

(56) References Cited

U.S. PATENT DOCUMENTS

| 5,336,616 A | * | 8/1994 | Livesey | ............. A01N 1/02 435/395 |
| 2010/0145444 A1 | | 6/2010 | Kishida et al. | |

(Continued)

FOREIGN PATENT DOCUMENTS

| CN | 1691950 | 11/2005 |
| CN | 203802502 | 9/2014 |

(Continued)

OTHER PUBLICATIONS

Pabittei et al., Laser-assisted vessel welding: state of the art and future outlook, Journal of Clinical and Translational Research 2015(2): 61-77.*

(Continued)

*Primary Examiner* — Jennifer M. H. Tichy
(74) *Attorney, Agent, or Firm* — Wenderoth, Lind & Ponack, L.L.P.

(57) ABSTRACT

A method of producing a decellularized transplantation material, wherein the method includes the steps of (a) harvesting a branch-bearing blood vessel from a vertebrate animal (a donor); (b) decellularizing the blood vessel; and (c) adhering, by a protein denaturation treatment, a portion (Continued)

where a branch has been excised to close the vessel. Also, a graft composition consisting of a biocompatible material that contains the decellularized transplantation material.

1 Claim, 3 Drawing Sheets (58) Field of Classification Search
USPC .......................................................... 600/36
See application file for complete search history.

(56) References Cited

U.S. PATENT DOCUMENTS

| | | | |
|---|---|---|---|
| 2014/0296847 A1* | 10/2014 | Chin | A61B 17/3417 606/41 |
| 2018/0296728 A1* | 10/2018 | Hiwatari | A61F 2/06 |

FOREIGN PATENT DOCUMENTS

| | | |
|---|---|---|
| CN | 104411816 | 3/2015 |
| JP | 60-501540 | 9/1985 |
| JP | 63-279832 | 11/1988 |
| JP | 2000-505315 | 5/2000 |
| JP | 2002-507907 | 3/2002 |
| JP | 2003-518981 | 6/2003 |
| JP | 2003-525062 | 8/2003 |
| JP | 2004-94552 | 3/2004 |
| JP | 2005-185507 | 7/2005 |
| JP | 2005-211480 | 8/2005 |
| JP | 2010-221012 | 10/2010 |
| JP | 2013-502275 | 1/2013 |
| WO | 97/26831 | 7/1997 |
| WO | 01/49210 | 7/2001 |
| WO | 2005/063316 | 7/2005 |
| WO | 2008/111530 | 9/2008 |
| WO | 2016/194895 | 12/2016 |

OTHER PUBLICATIONS

Funamoto et al., The use of high-hydrostatic pressure treatment to decellularize blood vessels, Biomaterial, vol. 31, (2010), pp. 3590-3595.*

International Search Report issued Aug. 7, 2018 in International (PCT) Application No. PCT/JP2018/020141.

Kawasaki et al., "Novel detergent for whole organ tissue engineering," Journal of Biomedical Materials Research Part A, Oct. 2015, vol. 103A, Issue 10, pp. 3364-3373.

Hee-Bung Park, "Energy-using surgical equipment and instruments", Park Hee-Bung Surgery, Dec. 8, 2014, http://pabc.net/page/s5/s1.php?cf=view&seq=48&pg=4%20(2014.12.08.%EC%9E%90%20%EA%B3%B5%ES%B0%9C)%20%EB%81%9D., with English machine translation.

* cited by examiner

METHOD FOR PRODUCING DECELLULARIZED MATERIAL FOR TRANSPLANTATION AND GRAFT COMPOSITION CONSISTING OF BIOCOMPATIBLE MATERIAL INCLUDING SAID MATERIAL

TECHNICAL FIELD

The present invention relates to a method of producing a decellularized material that can be used for transplantation and also relates to a graft composition consisting of a biocompatible material that contains this material.

BACKGROUND ART

Graft rejection by the graft recipient-side tissue is a problem for the transplantation of a graft derived from the biological tissue of another person. The development of artificial tissue is anticipated as a method for solving this problem. Various polymers have been investigated for the material here; however, due to the low compatibility between these materials and biological tissue, shedding and infection can be produced at the region where the graft is joined to the biological tissue. Thus, in order to improve the compatibility with biological tissue, art has been developed in which decellularized biological tissue, which is the supporting tissue remaining after the removal of the cells from biological tissue, is used.

The following properties, among others, are required of decellularized material: (i) strength as a graft, (ii) removal of the rejection-inducing DNA present in the decellularized tissue, and (iii) facile infiltration by autologous cells after transplantation. A variety of production methods have been investigated in order to obtain decellularized material that satisfies these requirements. For example, methods that use a surfactant (refer, for example, to Patent Documents 1 and 2), methods that use enzymes (refer, for example, to Patent Document 3), methods that use an oxidizing agent (refer, for example, to Patent Document 4), methods that employ a high hydrostatic pressure treatment (refer, for example, to Patent Documents 5 to 7), methods that employ a freeze-thaw treatment (refer, for example, to Patent Documents 8 and 9), and methods based on treatment with a hypertonic electrolyte solution (refer, for example, to Patent Document 10) are known.

CITATION LIST

Patent Document

[Patent Document 1] Japanese Patent Application Publication No. S60-501540
[Patent Document 2] Japanese Application Publication No. 2003-518981
[Patent Document 3] Japanese Application Publication No. 2002-507907
[Patent Document 4] Japanese Application Publication No. 2003-525062
[Patent Document 5] Japanese Patent Application Publication No. 2004-094552
[Patent Document 6] WO 2008/111530
[Patent Document 7] Japanese Application Publication No. 2013-502275
[Patent Document 8] Japanese Patent Application Publication No. 2005-185507
[Patent Document 9] Japanese Patent Application Publication No. 2005-211480
[Patent Document 10] Japanese Patent Application Publication No. 2010-221012

Non Patent Document

[Non-Patent Document 1] JOURNAL OF BIOMEDICAL MATERIALS RESEARCH A, October 2015 Vol. 103A, 10

SUMMARY OF INVENTION

Technical Problem

In order to maintain functionality as decellularized tissue, it is generally crucial that the surface state be preserved and thus that morphological damage to the tissue be suppressed to the greatest extent possible (for example, Non-Patent Literature 1). Even relatively minor damage has an effect on autologous cell infiltration. The present inventors have thus found that autologous cell infiltration is hindered when a suturing process, which is thought to inflict less damage on decellularized tissue, is performed. Based on these results, it is considered to be crucial that the suture regions in a graft composition derived from biological tissue be kept to the essential minimum.

Solution to Problem

Specifically, the branch portions must be excised and the vessel must be closed when a decellularized tissue obtained from a branch (branch blood vessel)-bearing blood vessel is used as a graft composition. It has been discovered that, when vessel closure is performed by carrying out a protein denaturation treatment as the means for closing the vessel at the part where a branch has been excised rather than using suturing, autologous cell infiltration at the decellularized tissue is not hindered and the tissue of the graft is regenerated.

The present invention thus provides a method of producing a decellularized transplantation material, including the steps of:
(a) harvesting a branch-bearing blood vessel from a vertebrate animal (a donor);
(b) decellularizing the blood vessel; and
(c) adhering, by a protein denaturation treatment, a portion where a branch has been excised to close the vessel.

The method of producing a decellularized transplantation material according to the present invention may further includes a step of excising a branch portion from the blood vessel harvested in step (a).

The present invention also provides a graft composition consisting of a biocompatible material, the biocompatible material containing a decellularized transplantation material wherein the decellularized transplantation material includes a vertebrate animal (donor)-derived blood vessel from which a branch has been excised and the decellularized transplantation material has at least one branch-excised portions where the vessel has been closed by protein denaturation.

Advantageous Effects of Invention

The production method according to the present invention can provide a decellularized transplantation material for a graft composition that facilitates the infiltration of autologous cells post-transplantation. In addition, the graft composition, which contains, in at least a portion thereof, the decellularized transplantation material provided by the production method according to the present invention, facilitates the infiltration of autologous cells post-transplantation and also makes it possible to function as normal biological tissue post-transplantation.

DESCRIPTION OF EMBODIMENTS

The method according to the present invention for producing a decellularized transplantation material will now be described.

A branch-bearing blood vessel is harvested from a vertebrate animal (donor) in the present invention.

The harvesting referred to here means the isolation of a branch-bearing blood vessel from the donor. In addition, the "branch-bearing blood vessel" refers to a blood vessel that in the donor exhibits branching, and also includes blood vessels from which a branch or branches is or are excised during harvesting.

There are no particular limitations on the vertebrate animal in the present invention, but since the blood vessel is preferably easily acquired, non-human animals are preferred with mammalian livestock and avian livestock being particularly preferred. The mammalian livestock can be exemplified by the cow, horse, camel, llama, donkey, yak, sheep, pig, goat, deer, alpaca, dog, raccoon dog, weasel, fox, cat, rabbit, hamster, guinea pig, rat, squirrel, and raccoon. The avian livestock can be exemplified by the true parrot, cockatoo, chicken, duck, turkey, goose, guinea fowl, pheasant, ostrich, emu, and quail. Among the preceding, the pig, rabbit, and cow are preferred based on the stability of supply.

Figure 1:
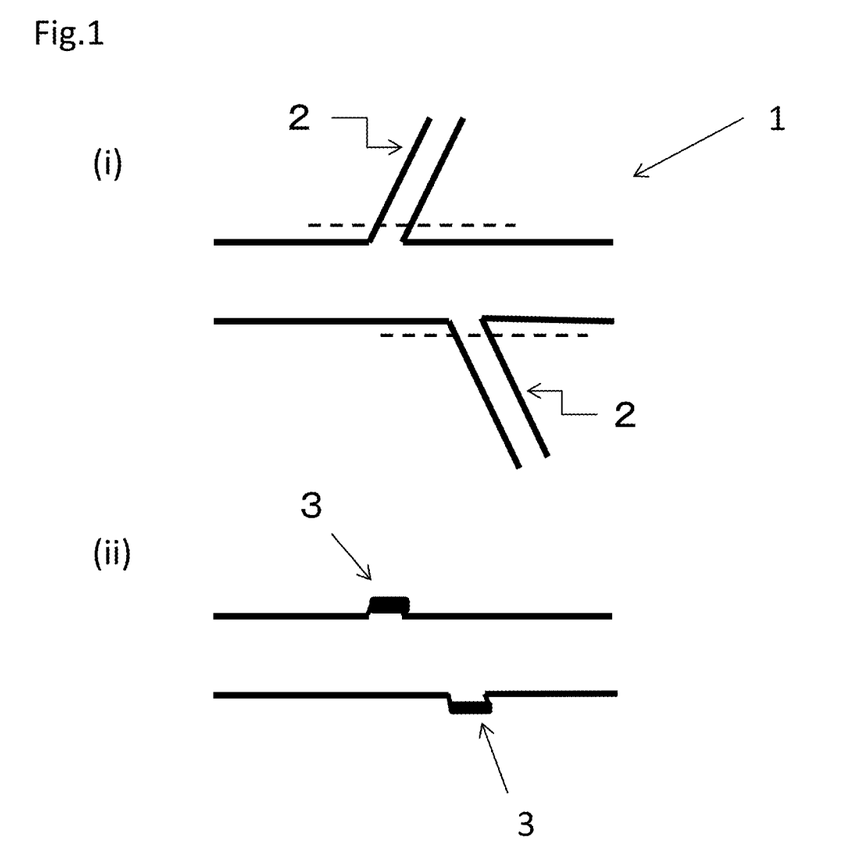
FIG. 1 is a schematic diagram of a branch-bearing blood vessel. 1 in (i) is a branch-bearing blood vessel; 2 is a branch portion (branch blood vessel); and the dashed line indicates an example of a position at which the branch portion is excised. The dashed line is preferably 1 mm to 2 mm away from the blood vessel. In another embodiment, the position of this dashed line may be 5 mm to several cm away from the blood vessel. 3 in (ii) indicates a protein-denatured region.

A branch-bearing blood vessel is used in the method according to the present invention of producing a decellularized transplantation material. This branch-bearing blood vessel refers to a blood vessel that has at least one or more branch portions (branch blood vessels), as shown in FIG. 1.

Since a blood vessel with a branch structure has a complicated shape, such a blood vessel is unsuitable for processing even when decellularized, and in addition, due to the branching structure, it has almost never been used in blood vessel transplantation applications. The present invention makes it possible to use a branch bearing blood vessel as an unbranched blood vessel by adhering the branch portions of the blood vessel to close the vessel. The significance of the ability to use a branch-bearing blood vessel as a graft composition, an application that has heretofore been quite problematic, is extremely consequential.

The branch-bearing blood vessel can be specifically exemplified by the internal thoracic artery, epigastric artery, gastro-omental artery, carotid artery, radial artery, intercostal artery, musculophrenic artery, femoral artery, deep femoral artery, aorta, ulnar artery, brachial artery, anterior tibial artery, posterior tibial artery, mesenteric artery, splenic artery, internal thoracic vein, anterior intercostal vein, azygos vein, hemiazygos vein, jugular vein, intestinal vein, femoral vein, saphenous vein, mesenteric vein, and splenic vein. Considering the physical characteristics of a graft composition (e.g., elongation, biocompatibility, and strength), arteries are preferred and the internal thoracic artery is more preferred.

With regard to the branch-bearing blood vessel, the vertebrate animal is anesthetized or euthanized and a part of the body, e.g., the thorax, abdomen, or leg, is then incised and the branch-bearing blood vessel to be harvested is excised. The methods heretofore used by the person having ordinary skill in the art may be used as such for the method of anesthesia or euthanasia.

The incision of the part of the vertebrate body may be made using a scalpel, scissors, or so forth as commonly used in animal experiments or surgery.

A scalpel, scissors, or so forth as commonly used in animal experiments or surgery may similarly be used to harvest the branch-bearing blood vessel. The use of an ultrasonic scalpel or electric scalpel is preferred for blood vessel excision. With these, the blood vessel may be excised while coagulating the blood, by ultrasonic vibration or high-frequency electric current at the location of blood vessel excision. The use of an ultrasonic scalpel is particularly preferred because this provides a favorable extent of protein denaturation of the excised portion.

In the present Description, "ultrasonic scalpel" and "ultrasonic vibration scalpel" are used as synonyms.

Electric scalpels usable for the present invention can be exemplified by the VIO series from Erbe Elektromedizin GmbH and the SHAPPER series from Senko Medical Instrument Mfg. Co., Ltd. Ultrasonic scalpels usable for the present invention can be exemplified by the Sonopet UST-2001 from Stryker Medical and the Harmonic scalpel from Ethicon Endo-Surgery.

The blood vessel harvested in step (a) may be in a condition in which branch portions have already been excised or may be in a condition in which branch portions remain at a sufficient length (for example, 5 mm to several cm). When branch portions remain at a sufficient length, these are excised as appropriate.

With regard to the length of a branch portion where the protein denaturation treatment is performed, a position separated by 1 mm to 10 mm from the bifurcation in the blood vessel is preferred, a position separated by 2 mm to 7 mm is more preferred, and a position separated by 3 to 5 mm is more preferred. Carrying out the protein denaturation treatment in this range makes it possible to minimize the effects associated with the denaturation treatment (alteration of properties and failure to stop blood flow, antithrombotic behavior, and so forth) when the decellularized transplantation material according to the present invention is deployed, and makes it possible to promote tissue regeneration.

A decellularization treatment is performed on the blood vessel harvested from the vertebrate animal. The decellularization treatment can be exemplified by surfactant treatments (Singelyn J. M., et al., Biomaterials, 2009, 30, 5409-5416; Singelyn J. M., et al., J. Am. Coll. Cardiol., 2012, 59, 751-763; Sonya B., et al., Sci. Transl. Med., 2013, 5, 173ra25), enzyme treatments, osmotic pressure treatments, freeze-thaw treatments, oxidizing agent treatments, and high hydrostatic pressure treatments (Sasaki S., et al., Mol. Vis., 2009, 15, 2022-2028; Yoshihide H., et al., Biomaterials, 2010, 31, 3941-3949; Seiichi F., et al., Biomaterials, 2010, 31, 3590-3595; Negishi J., et al., J. Artif. Organs, 2011, 14, 223-231; Japanese Patent No. 4,092,397; Republished International Patent Publication No. WO 2008-111530; and Japanese Patent Application Publication No. 2009-50297) and combinations of the preceding; however, the decellularization treatment is preferably carried out using a high hydrostatic pressure treatment.

With regard to the pressure during the execution of the high hydrostatic pressure treatment, a pressure that can rupture the cells and pathogens originating with the vertebrate animal donor is acceptable and can be selected as appropriate in conformity with the species of animal donor and type of blood vessel. The hydrostatic pressure is, for example, 2 to 1,500 MPa. Decellularization of the blood vessel is satisfactorily performed when the applied hydrostatic pressure is higher than 50 MPa. Due to this, 50 to 1,500 MPa is preferred, 80 to 1,300 MPa is more preferred, 90 to 1,200 MPa is still more preferred, and 95 to 1,100 MPa is most preferred.

The medium used to apply the high hydrostatic pressure can be exemplified by water, physiological saline, buffers, propylene glycol or an aqueous solution thereof, glycerol or an aqueous solution thereof, and aqueous saccharide solutions. The buffers can be exemplified by acetate buffers, phosphate buffers, citrate buffers, borate buffers, tartrate buffers, Tris buffers, HEPES buffers, and MES buffers. The saccharide in the aqueous saccharide solution can be exemplified by erythrose, xylose, arabinose, allose, talose, glucose, mannose, galactose, erythritol, xylitol, mannitol, sorbitol, galactitol, sucrose, lactose, maltose, trehalose, dextran, alginic acid, and hyaluronic acid.

The temperature of the medium in the high hydrostatic pressure treatment is not particularly limited as long as the temperature is one at which ice formation does not occur and the tissue is not damaged by the heat. Viewed in terms of the smooth execution of the decellularization treatment and also having little effect on the tissue, 0° C. to 45° C. is preferred, 4° C. to 40° C. is more preferred, 10° C. to 37° C. is still more preferred, and 15° C. to 35° C. is most preferred.

With regard to the length of the high hydrostatic pressure treatment, the decellularization treatment is inadequate when the time is too short, while a long treatment wastes energy. As a consequence, 5 minutes to 12 hours is preferred, 7 minutes to 5 hours is more preferred, and 10 minutes to 3 hours is still more preferred.

The adequacy of the decellularization can be checked by histological staining (hematoxylin-eosin stain) or by a determination of the remnant DNA.

In the case of blood vessels to which a high hydrostatic pressure is applied, the cells in the tissue are ruptured and the resulting cellular components are removed using a wash solution. This wash solution may be the same liquid as the medium used for application of the high hydrostatic pressure or may be a different wash solution, and a combination of a plurality of types of wash solutions may be used. The wash solution preferably contains a nuclease, organic solvent, or chelating agent. The nuclease enhances the efficiency of removal of the nucleic acid components from the blood vessel to which the hydrostatic pressure has been applied, while the organic solvent enhances the efficiency of lipid removal. The chelating agent, by deactivating the calcium ion and magnesium ion in the decellularized tissue, can prevent calcification when the decellularized tissue is applied to an affected part.

In the present invention, vessel closure is performed by carrying out a protein denaturation treatment on the portion where a branch has been excised. There are no particular limitations here on the means of carrying out protein denaturation, but, considered in terms of process convenience and efficiency and causing little tissue damage, the use of an ultrasonic scalpel or electric scalpel is preferred, while the use of an ultrasonic scalpel is preferred from the standpoints of low tissue damage and ensuring closure of the branch stump.

An ultrasonic scalpel has a structure in which a blade edge is mechanically ultrasonically vibrated. The biological tissue surrounding contact with the blade edge then produces frictional heat and the protein in the biological tissue is denatured. The open portion where the branch blood vessel has been excised is adhered and closed by this protein denaturation.

The aforementioned "vessel closure is performed by carrying out a protein denaturation treatment on the portion where a branch has been excised" also includes the case in which "branch excision" is performed at the same time as "vessel closure is performed by carrying out a protein denaturation treatment".

The frequency when the treatment is performed using ultrasound as described above is preferably 20 kHz to 100 kHz and more preferably about 30 kHz to about 60 kHz. The output is preferably 50 to 500 mA, more preferably 100 to 400 mA, and still more preferably 200 to 300 mA (for the use of 100 V AC).

The time for which the ultrasound treatment is performed varies with the frequency and output and is not particularly limited; however, it is preferably 0.1 second to 10 minutes, more preferably 1 second to 5 minutes, and still more preferably 3 to 60 seconds.

The individual steps are described in sequence in the following for the method according to the present invention of producing a decellularized transplantation material, including the steps of (a) harvesting a branch-bearing blood vessel from a vertebrate animal (a donor); (b) decellularizing the blood vessel; and (c) closing the vessel by adhering, by a protein denaturation treatment, a portion where a branch has been excised.

These steps (a), (b), and (c) in this embodiment are each not limited to the order given above.

For example, in addition to a case where the execution of step (a), step (b), and step (c) in the indicated order, step (c) may be carried out after step (a), followed by the execution of step (b). In another embodiment, a branch portion of the branch-bearing blood vessel may be excised prior to harvesting from the vertebrate donor animal; the portion where the branch has been excised may be subjected to a protein denaturation treatment; harvesting from the donor may be performed; and this may be followed by execution of the decellularization of step (b). An embodiment containing the sequence of step (c), step (a), and step (b) is thus encompassed by the present invention.

In another embodiment, a step (d) of excising the branch portion may also be included for the case in which a branch portion of the branch-bearing blood vessel harvested in step (a) remains in sufficient length (for example, the length of the branch portion is 5 mm to several cm). There is no particular limitation as to whether this step (d) is always carried out.

For example, the following is also possible: the sequence of step (a), step (d), step (b), and step (c), and the sequence of step (a), step (b), step (d), and step (c).

From the standpoint of enabling vessel closure without overlooking a branch blood vessel and providing a more efficient operation, it is more preferable that "branch excision" and "vessel closure is performed by carrying out a protein denaturation treatment" are performed in the present invention at the same time in step (c) and step (c) and step (a) are carried out successively. Also in this case, step (c) may be carried out again before and after step (b).

The present invention also provides a graft composition consisting of a biocompatible material that contains a decellularized transplantation material wherein the decellularized transplantation material consisting of a vertebrate animal (donor)-derived blood vessel from which a branch has been excised and the decellularized transplantation material has at least one branch-excised portions where the vessel has been closed by protein denaturation.

There are no particular limitations on the vertebrate animal for the graft composition according to the present invention, but since ease of blood vessel acquisition is advantageous, non-human animals are preferred with mammalian livestock and avian livestock being particularly preferred. The mammalian livestock and avian livestock here are the same as the livestock listed as specific examples of the mammalian livestock and avian livestock for use in the method according to the present invention for producing a decellularized transplantation material. Among these, the pig, rabbit, and cow are preferred based on the stability of supply.

With reference to the graft composition according to the present invention, the "blood vessel from which a branch has been excised" is a blood vessel, which is used to produce the decellularized transplantation material according to the present invention and is provided by the excision of a branch portion from a branch-bearing blood vessel. The same blood vessels used for the above-described production method can be used as this branch-bearing blood vessel, and, upon considering the physical characteristics of a graft composition (e.g., elongation, biocompatibility, and strength), arteries are preferred and the internal thoracic artery is more preferred.

The decellularized transplantation material used in the graft composition according to the present invention has a denatured-protein portion. Specifically, the location of excision of a branch portion assumes an open vessel state, and the open vessel portion can be closed by carrying out a protein denaturation treatment.

The specific method of the protein denaturation treatment is not particularly limited to being the same as for the above-described decellularized transplantation material, but an ultrasonic scalpel or electric scalpel can be used. The use of an ultrasonic scalpel is preferred because this causes little damage to the tissue.

The conditions with regard to the treatment time and ultrasound frequency for bringing about protein denaturation are the same for the graft composition according to the present invention as for the conditions for the treatment time and ultrasound frequency for the above-described method of producing a decellularized transplantation material.

With regard to the decellularized transplantation material used for the graft composition according to the present invention, the same decellularization treatment may be performed for the decellularization treatment as the decellularization treatment that has been described above, with the decellularization treatment preferably being performed by a high hydrostatic pressure treatment.

With regard to the pressure during execution of the high hydrostatic pressure treatment, a pressure that can rupture the cells and pathogens originating with the vertebrate animal donor is acceptable, and the treatment can be performed using the same hydrostatic pressure conditions as already described above. In addition, the medium used to apply the high hydrostatic pressure can be exemplified by water, physiological saline, buffers, propylene glycol or an aqueous solution thereof, glycerol or an aqueous solution thereof, and aqueous saccharide solutions, and the same media provided above as specific examples of the medium can be used as specific examples of each of the media here.

The graft composition according to the present invention consists of a prescribed biocompatible material. This "biocompatible" means that the graft does not induce toxicity or significant immunorejection when the graft is incorporated by the graft-recipient tissue.

The biocompatible material should be a solid and should not exhibit flowability, but is not otherwise particularly limited, and can be exemplified by non-resorbable polymers, absorbable polymers, metals, glasses, and ceramics.

The non-resorbable polymers can be exemplified by polyethylene, polyethylene terephthalate, polybutylene, polybutylene terephthalate, polypropylene, acryl, polyamideimide, polyetheretherketone, polyaryletherketone, polycarbonate, polyamide, polyvinyl fluoride, polyvinylidene fluoride, polymethyl methacrylate, and combinations and equivalents of the preceding; however, there is no limitation to the preceding.

The aforementioned absorbable polymer may be a synthetic polymer or a natural polymer, and can be exemplified by polyamino acids, polyamide, and fatty acid polyesters and natural polymers such as collagen, elastin, hyaluronic acid, laminin, gelatin, keratin, chondroitin sulfate, and decellularized tissues.

The metals can be exemplified by tantalum, tantalum alloys, stainless steel, titanium, titanium alloys, and cobalt-chromium alloys, and the biocompatible metals heretofore used in, for example, medical devices, can be used.

The glasses and ceramics can be exemplified by phosphate salts such as tetracalcium phosphate, alpha- and beta-tricalcium phosphates, octacalcium phosphate, hydroxyapatite, substituted apatite, monetite, metaphosphate salts, pyrophosphate salts, and phosphate glasses, and by carbonate salts, sulfate salts and oxides of calcium and magnesium and combinations of the preceding. However, there is no limitation to the preceding.

The graft composition according to the present invention consisting of a biocompatible material that contains in at least a portion thereof the prescribed decellularized transplantation material. This "contains for at least a portion thereof" means that one or more or a plurality of decellularized transplantation materials can be present in the biocompatible material. Viewed from the standpoint of more effectively achieving the infiltration of autologous cells, the biocompatible material more preferably consists of only decellularized material.

The graft composition according to the present invention can function post-transplantation as a portion of a biological tissue. It can function in particular as a blood vessel substitute for transplantation service.

Examples

1. Preparation of Decellularized Porcine Internal Thoracic Arteries
Harvesting of Porcine Internal Thoracic Arteries (Treatment of Branch Blood Vessels)

The thorax of a 3 to 4 month-old hog (specific pathogen free (SPF) pig, female, body mass of approximately 50 kg) was opened under anesthesia and the interior thoracic artery was exposed. The internal thoracic artery was detached (harvested) from the thoracic wall while contacting and coagulating the branch blood vessels using 55,500 Hz and an output level of 2 for the settings on an ultrasonic scalpel (Harmonic Scalpel II, Harmonic SYNERGY, Ethicon Endo-Surgery).

Figure 2:
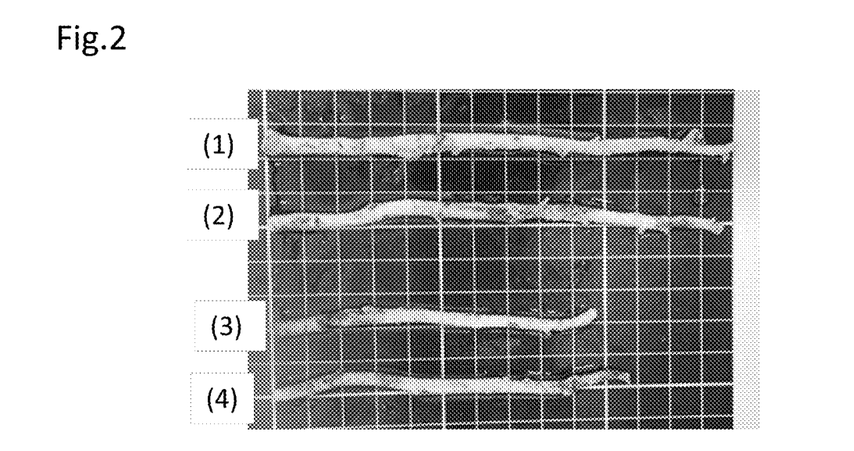
FIG. 2 is a diagram that shows internal thoracic artery segments in the examples; these segments were harvested from pigs and the branch portions have been excised. The internal thoracic artery segment in (3) in the diagram was used as a comparative example in the examples provided below.
Figure 3:
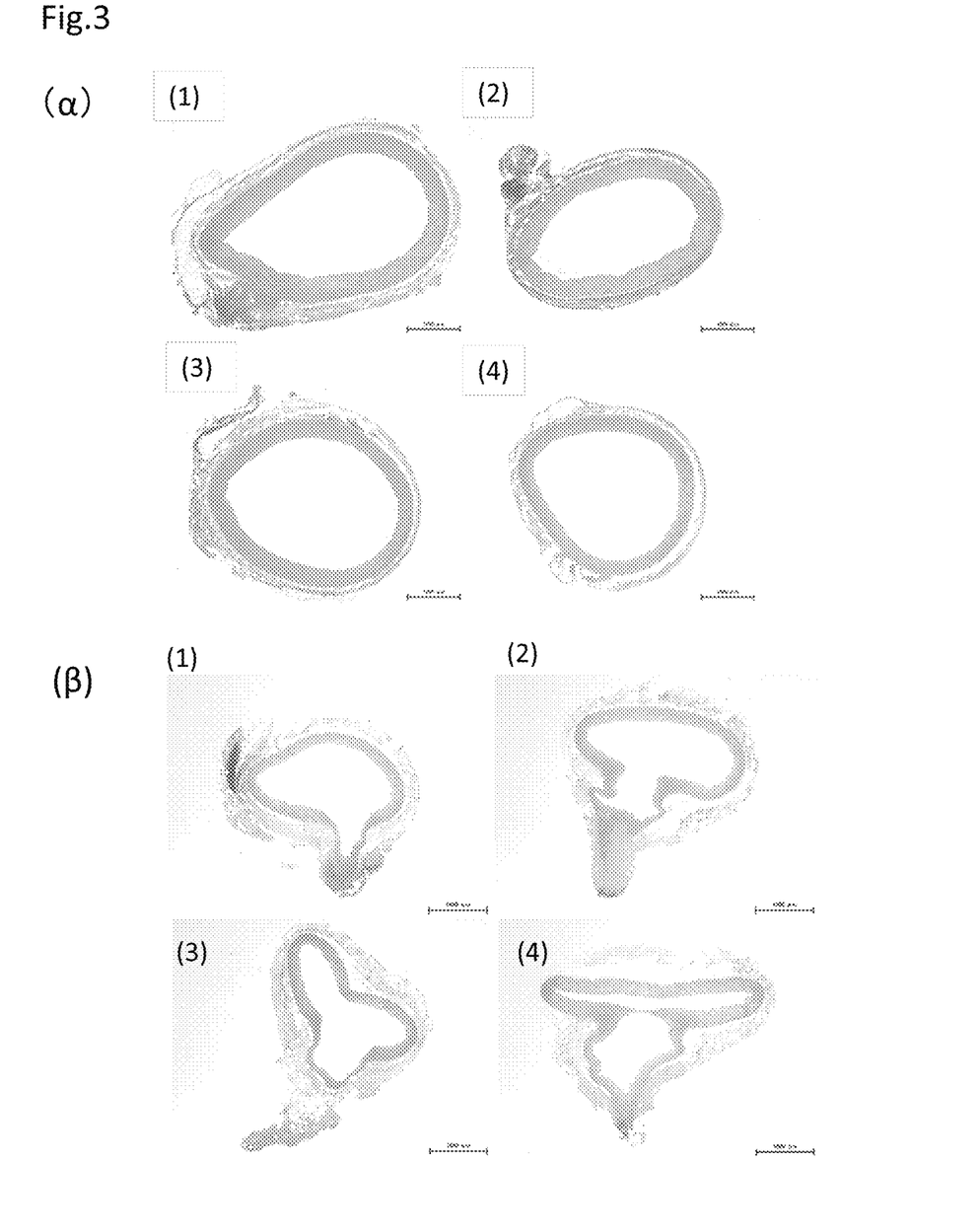
In FIG. 3, (α) in the diagram refers to enlarged photographs of hematoxylin eosin-stained cross sections of harvested porcine internal thoracic artery segments. (β) refers to enlarged photographs of cross sections of decellularized transplantation materials provided by the decellularization of harvested porcine internal thoracic artery segments and hematoxylin.eosin staining. The photographs reveals that decellularization has occurred and nucleic acid is not present. The scale bar is 1000 m in each case. The internal thoracic artery segment in (3) in the diagram was used as a comparative example in the examples provided below.

Four internal thoracic arteries were harvested from two pigs.
2. Observation of the Porcine Internal Thoracic Arteries The length and internal diameter of the four harvested porcine internal thoracic arteries were measured. These were as follows: (1) length: 140 mm, internal diameter: 3.2 mm, (2) length: 135 mm, internal diameter: 2.6 mm, (3) length: 95 mm, internal diameter: 2.9 mm, (4) length: 105 mm, internal diameter: 2.8 mm. The obtained porcine internal thoracic arteries (1) to (4) are given in FIG. 2. Their cross sections (HE stain) are given in FIG. 3.
3. Decellularization Treatment of the Porcine Internal Thoracic Arteries
[Reagents Used]
DNs Solution Otsuka Physiological Saline containing 50 mg/L DNase I (Roche, Grade II) and 2.55 g/L $MgCl_2 \cdot 6H_2O$ (Wako, JIS Special Grade)
EtOH Solution A solution of ethanol (Japanese Pharmacopeia) and Otsuka Physiological Saline prepared to give a volume ratio of 80%

Citric Acid Solution

A solution prepared by the addition of trisodium citrate dihydrate (Calbiochem, Molecular Biology Grade) and anhydrous citric acid (Wako, Special Grade) to Otsuka Physiological Saline and adjustment to pH 7.4.

The porcine internal thoracic arteries were treated with a superhigh hydrostatic pressure instrument (Dr. Chef, Kobe Steel, Ltd.) using water as the medium. The superhigh hydrostatic pressure treatment was performed using the following conditions: applied pressure=600 MPa, pressure rise time=9 minutes, pressure hold time=120 minutes, pressure release time=9 minutes, pressurization medium temperature=30° C.

After the superhigh pressure treatment, a 4-day wash was carried out with the 50 mg/L DNase I solution, a 3-day wash was carried out with the EtOH solution, and a 4-day wash was carried out with the citric acid solution to complete the decellularization.

With regard to the decellularization, hematoxylin-eosin staining (also referred to as HE staining in the following) was carried out and the absence of nucleic acid in the HE-stained section image was confirmed by microscopic observation.

HE staining uses two stains, i.e., hematoxylin and eosin, and is a method of differentially staining the cell nucleus and tissues and components other than the nucleus: hematoxylin stains the nucleus to dark blue, while eosin stains the cytoplasm, fibers, and red blood cells to pink.
4. Measurement of the Pressure Resistance After decellularization, an end of each particular porcine internal thoracic artery was pinched with a clamp and physiological saline was injected from the other end using a 20-mL syringe and the pressure resistance was measured. Excluding the aforementioned (3), the decellularized transplantation material from porcine internal thoracic arteries (1), (2), and (4) had a pressure resistance of at least 150 mmHg.

With (3), some of the branched portions were not closed off and leakage by the physiological saline could be observed.

The pressure resistance was measured as follows: physiological saline was injected into the porcine internal thoracic artery at a rate of 3 mL/min from a 20-mL syringe using a syringe pump (YSP-101), and the pressure at this time was measured using a digital pressure meter (KDM30).

In the ensuing experiments, (1), (2), and (4) are designated as examples and (3) is designated as a comparative example.
5. Suturing the Comparative Example Blood Vessel In the case of the decellularized transplantation material (3), the branch vessel-excised portions where physiological saline leakage had been observed were ligated with 6-0 proline thread. Ligation was performed by passing the suture thread into the tunica externa portion of the blood vessel and then tying off the tubular part of the branch from the outside.
6. Long-Term Transplantation of Decellularized Porcine Internal Thoracic Artery (Graft Composition Comprising Decellularized Transplantation Material) to Rabbit Aorta Transplantation Method Pentobarbital sodium hydrochloride (product name: Somnopentyl (registered trademark), 0.2 mL), physiological saline (1.8 mL/rabbit), and medetomidine hydrochloride (product name: Dorbene Injection, 1 mL) were injected subcutaneously into rabbits (breed: Japanese white rabbit, 5 months old, male) with a body mass of 3.70 to 4.00 kg. After confirmation of immobilization, the abdominal skin was shaved. Isoflurane inhalation (2% during induction, 1% during surgery) was performed as inhalation anesthesia, and, after retention on a holding table, the skin was disinfected with gauze soaked with a povidone-iodine preparation. A lidocaine injection solution diluted 3-fold with physiological saline (product name: Xylocaine (registered trademark)) was then injected subcutaneously in the abdomen, and an infusion line was run from the ear vein and Solita (registered trademark) T-3 was injected intravenously. Using an electric scalpel and scissors, the skin and peritoneum were cut open to expose the abdominal aorta, and 1000 units of heparin (1000 units/mL heparin, 1 mL) were intravenously injected from the infusion line. The elapse of 3 minutes after the intravenous heparin injection was then confirmed and the proximal side of the abdominal aorta was blocked. After inserting a shunt tube into the abdominal aorta, the blood flow block was released. While securing the blood flow with the shunt tube, the decellularized porcine internal thoracic artery and proximal abdominal aorta part were anastomosed by end-to-side anastomosis using 8-0 proline thread. The decellularized porcine internal thoracic artery and the distal abdominal aortic part were anastomosed in the same manner to prepare a bypass blood vessel. In addition, the abdominal aorta between the proximal anastomosis and distal anastomosis was ligated with 6-0 proline thread to direct blood flow to the bypass blood vessel. After the transplantation of the decellularized porcine internal thoracic artery, the abdomen was closed by suturing the peritoneal membrane with 4-0 PDS thread, suturing the muscle layer with 2-0 PDS, and suturing the skin with 4-0 PDS thread. 0.5 mL of Baytril (registered trademark) was administered as an antibiotic, and atipamezole hydrochloride (product name: Atipame Injection, 1 mL) was injected subcutaneously in the thigh as a medetomidine hydrochloride antagonist. After confirmation of awakening, the rabbit was transferred to a kennel cage.

Necropsy

Necropsy was performed on the rabbits at one or three months after transplantation of the decellularized porcine internal thoracic artery. Without running an infusion line from the rabbit, the abdominal aorta (transplanted decellularized porcine internal thoracic artery) was exposed using the same method as at the time of transplantation. Vascular patency and thrombus formation were then evaluated. The vascular patency was evaluated by cutting the distal side of the abdominal aorta and determining the presence or absence of bleeding. Hemorrhage was confirmed in all samples, which indicated that the blood vessels were patent. After the evaluation of vascular patency, the animal was sacrificed by injecting pentobarbital sodium (Somnopentyl (registered trademark), 5 mL) into the ear vein. After cardiac and respiratory arrest, the decellularized porcine internal thoracic artery was removed. The interior of the decellularized porcine internal thoracic artery was washed with physiological saline, after which an incision was made in the longitudinal direction and thrombus formation was visually observed. There was no thrombus adhesion to the lumen surface of the decellularized porcine internal thoracic artery and a high antithrombotic behavior was demonstrated. Here, "patency" means that an open condition is maintained without blockage of the blood vessel lumen.

Pathology Specimen Preparation

Pathology specimens of the transplanted decellularized porcine internal thoracic artery were prepared by New Histo. Science Laboratory Co., Ltd. Here, HE-stained sections and Elastica van Gieson (EVG)-stained sections, prepared by carrying out staining with the Elastica van Gieson stain (also referred to herebelow as the EVG stain), were prepared in regions of the decellularized porcine internal thoracic artery that enabled checking of the tissue structure of the branch blood vessel portion that had been closed with the ultrasonic scalpel or 6-0 proline thread. Specifically, sections are continuously taken in the longitudinal direction of the blood vessel at thicknesses of about 5 µm to produce sections at regions that enabled checking of the tissue structure of the branch blood vessel portion that had been closed with the ultrasonic scalpel or 6-0 proline thread.

EVG staining is a staining method that identifies elastic fibers, and, for connective tissue, it can differentially stain elastin to a blackish purple and collagen to a reddish purple.

Figure 4:
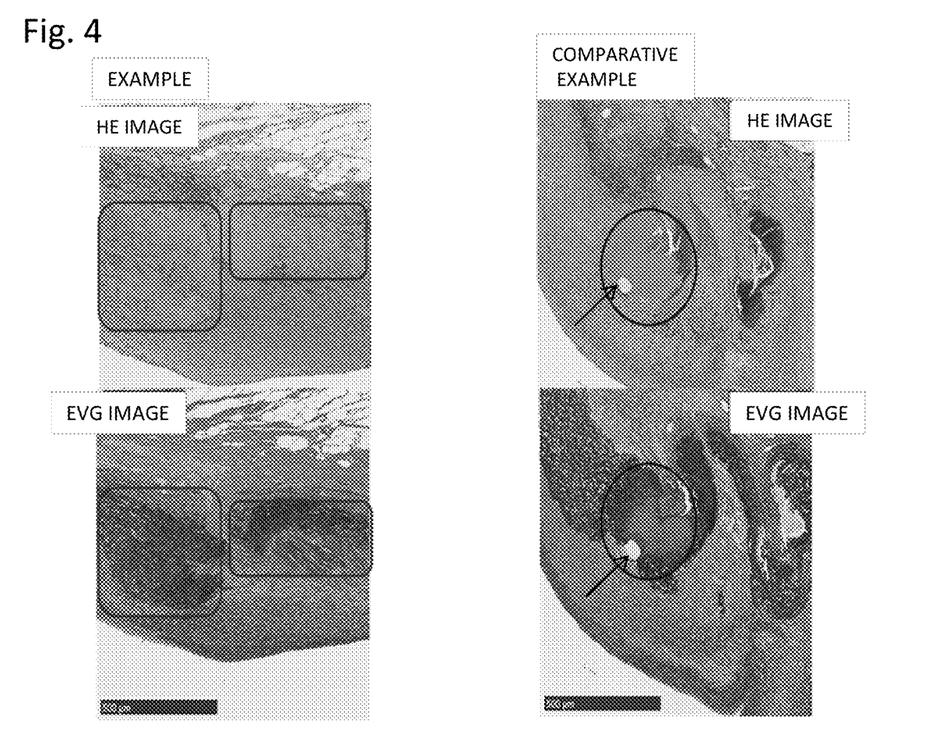
FIG. 4 contains enlarged photographs provided by transplantation into the rabbit of a decellularized porcine internal thoracic artery segment, i.e., a decellularized transplantation material, and after three months staining a section thereof with hematoxylin-eosin stain (HE stain) or Elastica van Gieson stain (EVG stain). In the comparative example, the small white circle designated by the arrow in the encircled region is the footprint of a traversing proline thread. The proline thread runs perpendicular to the plane of the paper. The photograph reveals that the infiltration of cells is not observed in the periphery around the passage of the proline thread. The scale bar in each case represents 500 µm.

The HE-stained image and the EVG-stained image (3 months) for an example sample and the HE-stained image and EVG-stained image (3 months) for the comparative example sample are given below (FIG. 4). In the example sample, it is shown that cells have also infiltrated into the decellularized porcine internal thoracic artery tissue region stained to blackish purple by EVG staining. In the comparative example sample, on the other hand, no cell infiltration was observed in the decellularized porcine internal thoracic artery tissue region stained to blackish purple by EVG staining.

Figure 5:
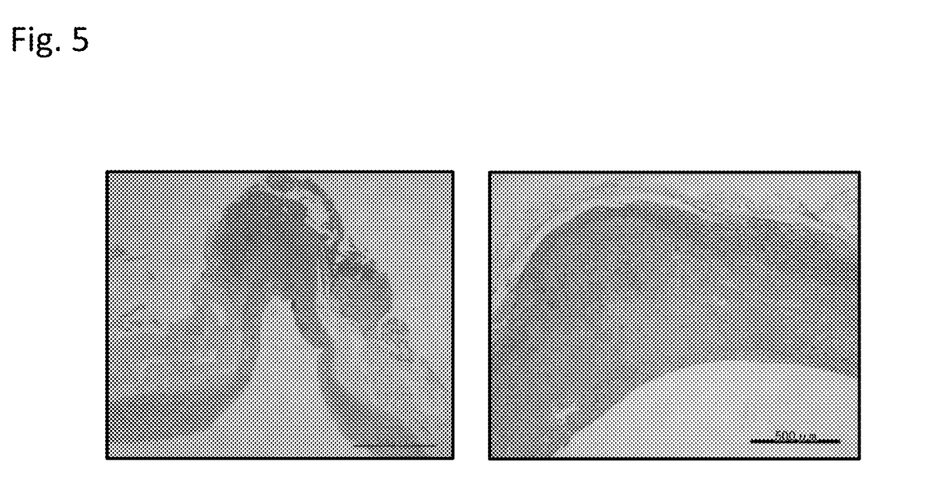
In FIG. 5, the left one is an enlarged photograph of a section of a branch portion, before transplantation, provided by the HE staining of a decellularized porcine internal thoracic artery segment, i.e., a decellularized transplantation material according to the present invention. The right one is an enlarged photograph of a section of an HE-stained branch portion one month after transplantation. Cell infiltration post-transplantation is observed. The scale bar in each case represents 500 µm.

Also, in an example sample, the finding was made that the level variation in the branched blood vessel was covered with rabbit cells at a stage of one month after transplantation (FIG. 5).

7.

Using distributed block meat of hog origin, the internal thoracic artery was detached (harvested) from the thoracic wall while contacting and coagulating the branch blood vessels using 55,500 Hz and output levels of 5 and 2 for the settings on an ultrasonic scalpel (EES Generator, Harmonic SYNERGY, Harmonic FOCUS+, <the blue hand piece was used>, Ethicon Endo-Surgery). Coagulation of the branched blood vessels was performed at a position 3 to 5 mm away from the blood vessel bifurcation, and five internal thoracic arteries were detached (harvested). After a decellularization treatment was performed by the method described in "3" above, the pressure resistance was measured by the method described in "4" above. A pressure resistance of at least 250 mmHg was confirmed for all five samples as a result.

REFERENCE SIGNS LIST

1 Branch-bearing blood vessel
2 Branch portion (branch blood vessel)
3 Protein-denatured region

The invention claimed is:
1. A method of producing a decellularized transplantation material, comprising steps of:
  (a) harvesting a branch-bearing blood vessel from a donor vertebrate animal;
  (b) decellularizing the branch-bearing blood vessel; and
  (c) adhering, by a protein denaturation treatment, a portion of the branch-bearing blood vessel where a branch has been excised to close the branch-bearing blood vessel,
  wherein the steps are performed in the following sequence:
  step (c), followed by step (a), followed by step (b), and after the steps (a), (b) and (c), a step of measuring a pressure resistance of the branch-bearing blood vessel to confirm that the closed portion of the branch-bearing blood vessel where the branch had been excised has a pressure resistance of 150 mmHg or more, wherein the protein denaturation treatment is performed on the portion of the branch-bearing blood vessel where the branch has been excised at a position 3 mm to 5 mm from a bifurcation in the branch-bearing blood vessel, wherein the protein denaturation treatment is an ultrasound vibration treatment, and wherein the decellularizing the branch-bearing blood vessel of step (b) contains a high hydrostatic pressure treatment in which a hydrostatic pressure of 50 to 1,500 MPa is applied.

* * * * *